United States Patent [19]
Gigliotti, Jr. et al.

[11] Patent Number: 5,445,688
[45] Date of Patent: Aug. 29, 1995

[54] METHOD OF MAKING ALLOY STANDARDS HAVING CONTROLLED INCLUSIONS

[75] Inventors: Michael F. X. Gigliotti, Jr., Scotia; Robert S. Gilmore, Burnt Hills; Lee C. Perocchi, Schenectady, all of N.Y.

[73] Assignee: General Electric Company, Schenectady, N.Y.

[21] Appl. No.: 205,235

[22] Filed: Mar. 3, 1994

[51] Int. Cl.⁶ .................................... C22F 1/18
[52] U.S. Cl. ..................... 148/527; 148/421; 228/165; 228/262.71
[58] Field of Search ............... 148/527, 421; 75/338, 75/342; 428/660, 661; 228/165, 198, 262.71

[56] References Cited

U.S. PATENT DOCUMENTS

| | | | |
|---|---|---|---|
| 377,316 | 1/1888 | Marshall | 428/614 |
| 3,419,952 | 9/1966 | Carlson | 29/471.3 |
| 3,663,723 | 9/1969 | Persson | 156/179 |
| 3,686,081 | 1/1970 | Butter et al. | 402/16 |
| 3,737,976 | 6/1973 | Lieberman et al. | 29/470.1 |
| 3,847,558 | 11/1974 | Trabocco et al. | 29/191.4 |
| 3,874,855 | 4/1975 | Legrand | 29/191.2 |
| 4,409,278 | 10/1983 | Jochym | 228/198 |
| 4,413,766 | 11/1983 | Webster | 228/123 |
| 4,731,115 | 3/1988 | Abkowitz et al. | 428/660 |
| 4,816,347 | 3/1989 | Rosenthal et al. | 428/615 |
| 4,857,411 | 8/1989 | Yamaguchi et al. | 228/165 |
| 4,867,644 | 9/1989 | Wright et al. | 416/230 |
| 4,978,585 | 12/1990 | Ritter et al. | 428/614 |
| 5,070,591 | 12/1991 | Quick et al. | 75/342 |
| 5,104,460 | 4/1992 | Smith, Jr. et al. | 428/660 |
| 5,260,137 | 11/1993 | Rosenthal et al. | 428/608 |
| 5,273,204 | 12/1993 | Dalal et al. | 228/165 |
| 5,290,332 | 1/1994 | Chatterjee et al. | 428/660 |

*Primary Examiner*—John Sheehan
*Attorney, Agent, or Firm*—Edmund P. Anderson; James Magee, Jr.

[57] ABSTRACT

A method of making metal alloy articles having inclusions which are predetermined and controlled with respect to their size, shape, composition, crystal structure and location and orientation within the article is disclosed. In a preferred embodiment, the method of making is directed toward titanium alloy articles containing synthesized hard-alpha inclusions of titanium/nitrogen, titanium/oxygen and titanium/oxygen/nitrogen alloys.

11 Claims, 7 Drawing Sheets fig. 1 fig. 1a fig. 2a fig. 2b fig. 2c fig. 3a fig. 3b fig. 3c fig. 4a fig. 4b fig. 4c fig. 5 fig. 5a fig. 6 fig. 7

METHOD OF MAKING ALLOY STANDARDS HAVING CONTROLLED INCLUSIONS

BACKGROUND OF THE INVENTION

This invention relates generally to the development of a method for making articles from metal alloys which have predetermined inclusions that are controlled with respect to their size, shape, composition and crystal structure, and also with respect to their location and orientation within the article, such as reference standards. Specifically, it relates to a method for making titanium alloy reference standards having brittle, hard, alpha-phase titanium inclusions which are controlled with respect to the factors described above.

The usage of many metal alloy systems is limited by the presence of certain metallic or intermetallic inclusions which often represent carbide, oxide, nitride, sulfide or other compounds of one or more of the alloy constituents, and which result from natural impurities associated with the alloy constituents, processing of the alloy or other sources. However, such inclusions are very often difficult to detect, and if detectable are difficult to characterize quantitatively using techniques such as ultrasound analysis because of their generally random nature (e.g. size, shape, orientation, location, composition, crystal structure). One example is brittle, "hard-alpha" inclusions found in titanium alloys. This form of titanium is stabilized by locally high concentrations of embrittling elements such as nitrogen and oxygen. Improved ability to detect small, hard-alpha titanium inclusions would permit more efficient designs of high temperature gas turbines and their components. However, naturally-occurring hard-alpha inclusions are rare in commercially produced titanium alloy components. The number of such inclusions has been reported to average about one per million pounds of titanium alloy produced. Also, hard-alpha inclusions are not generally found naturally in suitable forms to permit the development of new detection and inspection techniques, or the calibration of existing analytical equipment, so as to improve the ability or probability of detecting such inclusions, because the development of reliable detection techniques for inclusions such as hard-alpha inclusions typically requires characterization of several of their physical properties over a range of anticipated compositions and morphologies. For ultrasound techniques, this characterization might include the measurement of differential sound velocities, reflectance and density as a function of inclusion composition, size, shape, orientation and location, and then relating such measurements to detectability of the inclusions. Characterization is also often complicated by the fact that thermomechanical processing, such as forging and rolling, tends to crack the frequently brittle inclusions such that the characterization of their detectability is made ambiguous, because the presence of the crack is more detectable, using standard techniques such as ultrasound detection, than the presence of the inclusion.

Prior art methods for making alloys with controlled inclusions have included drilling holes or creating other mechanical discontinuities in articles made from an alloy of interest. However, there are major deficiencies with such methods. Mechanical discontinuities present the largest change possible in the physical characteristics of a material (e.g. for ultrasound measuring techniques, the speed of sound and reflectance) while actual inclusions, such as hard-alpha titanium within a titanium alloy, typically exhibit much less difference in physical characteristics in comparison with the alloy in which it is located. Thus, void-like or crack-like discontinuities are easier to detect than inclusions such that calibrating detection equipment from these discontinuities or inclusions which also contain these discontinuities, may not necessarily yield accurate extrapolations regarding the detectability of such inclusions.

SUMMARY OF THE INVENTION

The invention comprises a method of making an article from a metal or metal alloy so as to have a controlled, predetermined inclusion, or distribution of inclusions, each have a predetermined composition, morphology and geometry. In a preferred embodiment, the invention comprises a method of making titanium alloy articles containing synthesized hard-alpha inclusions of titanium/nitrogen, titanium/oxygen and titanium/oxygen/nitrogen alloys, each having a predetermined size, shape, composition, crystal structure and location and orientation within the article.

The method includes: A method for forming a titanium alloy preform having a reference surface and containing at least one inclusion having a predetermined composition, shape and size and also having a predetermined orientation to and location from the reference surface, comprising the steps of: selecting a first titanium alloy preform and a second titanium alloy preform each having a predetermined composition of alloying constituents and a bonding surface, wherein at least one of the first alloy preform and the second alloy preform have at least one reference surface; forming at least one cavity having a predetermined size and shape in the first titanium alloy preform; placing an inclusion material from the group consisting of a nitride, oxide, or carbide of titanium, or any combination thereof, and having a predetermined composition into the cavity; placing the bonding surfaces of the first titanium alloy preform and the second titanium alloy preform in touching contact; and applying a means for heating and a means for pressing the first titanium alloy preform and the second titanium alloy preform together for a time sufficient to form an inclusion and a metallurgical bond between the inclusion and the first titanium alloy preform and between the bonding surfaces of the first titanium alloy preform and the second titanium alloy preform, wherein the inclusion has a predetermined orientation to and distance from the at least one reference surface.

A significant feature of this method is that it permits the development of a metal alloy article which has physical properties of the inclusion, such as hard-alpha titanium inclusions in titanium alloy articles which do not primarily comprise the brittle, hard-alpha titanium phase. This feature provides a significant advantage in that it provides a method of producing articles with inclusions which are predetermined, and which may be pre-characterized, and which make possible research directed at developing techniques to detect and characterize such inclusions, so as to permit the calibration of instruments used for their detection and characterization. This advantage also makes possible the consideration of many options for improving metal alloys, comprising: seeking to control the incidence of inclusions of a particular type (e.g. shape, size, composition, crystal structure, location, orientation); seeking to ensure that known inclusions of a particular type do not exist in a completed article, or in the alternative that they will not interfere with the intended function of the article; and seeking to reduce or eliminate inclusions of a particular type by modifying alloy processing or fabrication techniques.

Therefore, one object of the present invention is to provide a method for making metal alloy articles with predetermined inclusions, such as titanium alloy articles with hard-alpha titanium inclusions having a known size, shape, composition and crystal structure and which have a known location and orientation within the article; or any combination of known characteristics.

Another object of the present invention is that to provide a method of making metal alloy articles having inclusions, such as titanium alloy articles with hard-alpha inclusions, which include the range of anticipated structures, compositions and geometries of both the article and the inclusion, in order to characterize the physical behaviors of the most significant combinations of these factors.

BRIEF DESCRIPTION OF THE DRAWINGS

FIG. 1a is a cross-sectional plan view of the article of FIG. 1a viewed at section plane 1a.

FIG. 5a is an exploded cross-sectional plan view of the article of FIG. 5 along plane 5a.

In these drawings, common numbering has been used in the various figures to represent the same or similar elements. Distinct numbers have been assigned to elements whose for may vary from one embodiment to another of the method of the present invention.

DETAILED DESCRIPTION OF THE INVENTION

This invention is related to the invention disclosed in co-pending application Ser. No. 08/205,234, filed on Mar. 3, 1994, which is hereby incorporated by reference.

In general, Applicants have determined that various types of inclusions can be synthesized in an article formed from a pure metal or metal alloy, and herein disclose several specific embodiments of this invention. These synthesized inclusions comprise materials such as oxides, nitrides, carbides and sulfides of an alloying constituent or constituents used in a particular alloy, or complex combinations of these materials which further may comprise various morphologies including, for example, both distinct phases and solid solutions. These synthetic inclusions can be made so as to be representative of inclusions which result naturally during the manufacture and fabrication of articles from a particular alloy system or systems.

Figure 1:
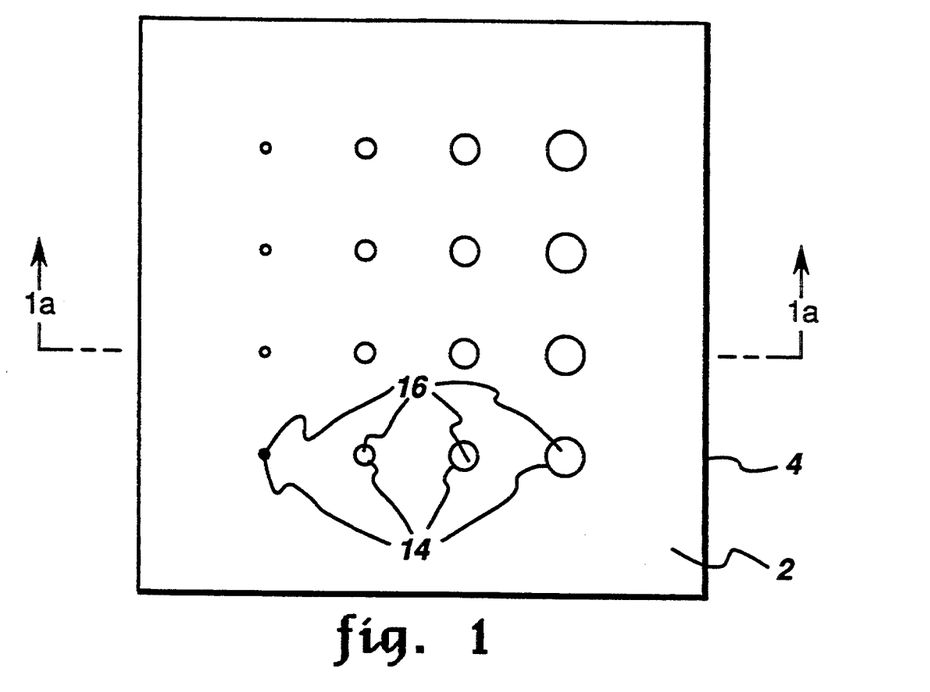
FIG. 1 is a top view of an article of the present invention.
Figure 1A:
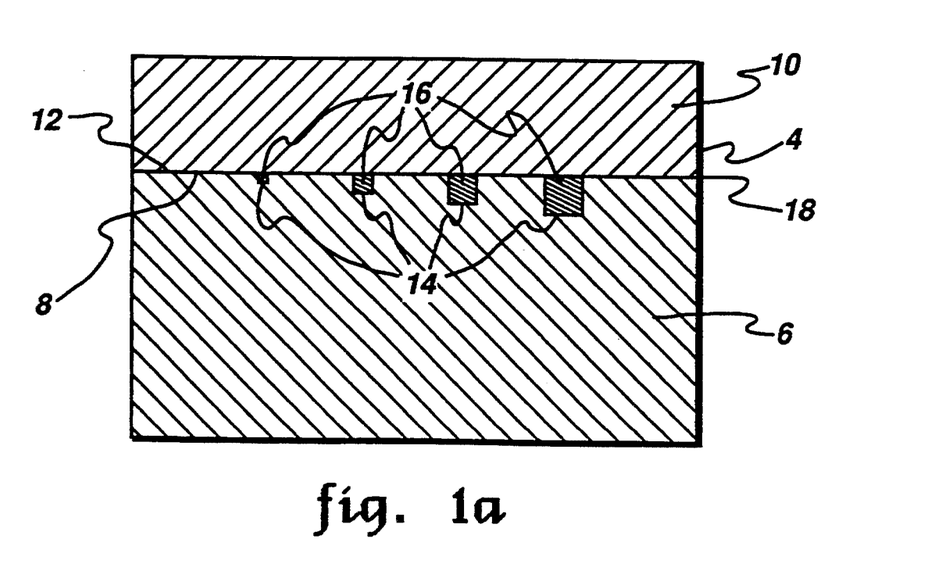

In particular, Applicants have synthesized hard-alpha titanium inclusions in articles formed from Ti—6A1-4V (Ti64), an alloy which is representative of titanium alloys generally. FIGS. 1 and 1a illustrate a completed article 2 made from a Ti—6A1-4V alloy in the form of rectangular block 4. Block 4 comprises a metal alloy matrix formed from first alloy preform 6, second alloy preform 10, and plurality of inclusions 16. First alloy preform 6 and second alloy preform 10 comprise plates of a Ti64 alloy. Inclusions 16 comprise Ti—N—O alloys as described in greater detail below. FIG. 1a also illustrates bond layer 18 resulting from the method used in a preferred embodiment to bond first alloy preform 6 and second alloy preform 10.

Referring again to FIGS. 1 and 1a, another way of characterizing Applicants invention is that article 2 as illustrated in the form of block 4 is in effect an alloy preform having a predetermined composition of alloying constituents which in a preferred embodiment is Ti64. Block 4 has at least one reference surface 20 with reference to which inclusions 16, having a predetermined size, shape and composition, are located and oriented. In the present invention, inclusion 16 must comprise at least one metallic inclusion, but in the illustrated preferred embodiment of FIG. 1 and 1a includes plurality of inclusions 16 made from Ti—N—O alloys, as described more fully below.

Figure 2A:
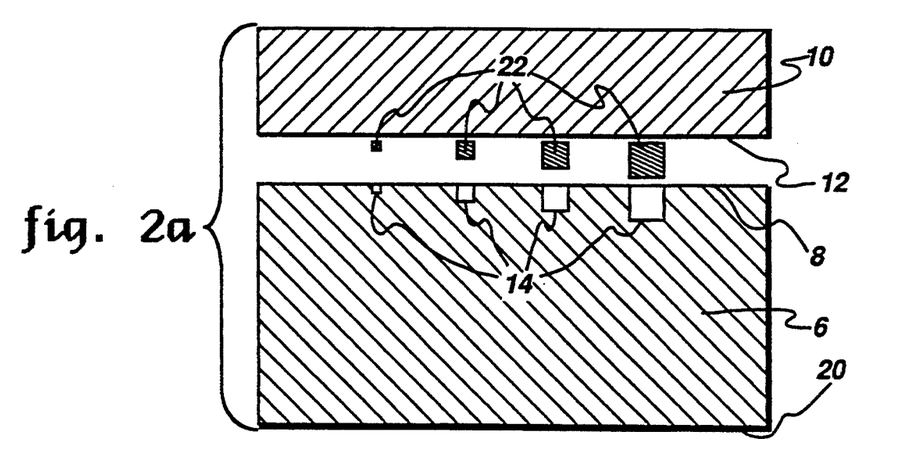
FIG. 2a is an exploded, cross-sectional plan view of certain elements of an article of the present invention which partially illustrate a first embodiment of the method of making.
Figure 2B:
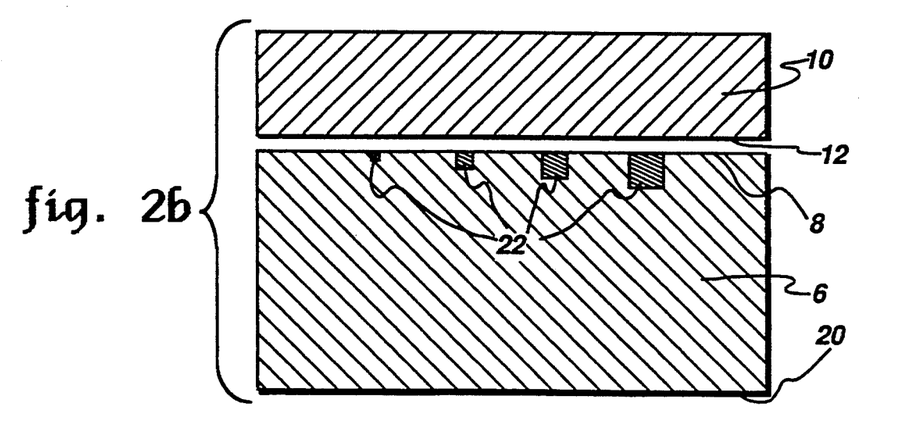
FIG. 2b is a view of the elements of FIG. 2a and their arrangement which further illustrate the method of making.
Figure 2C:
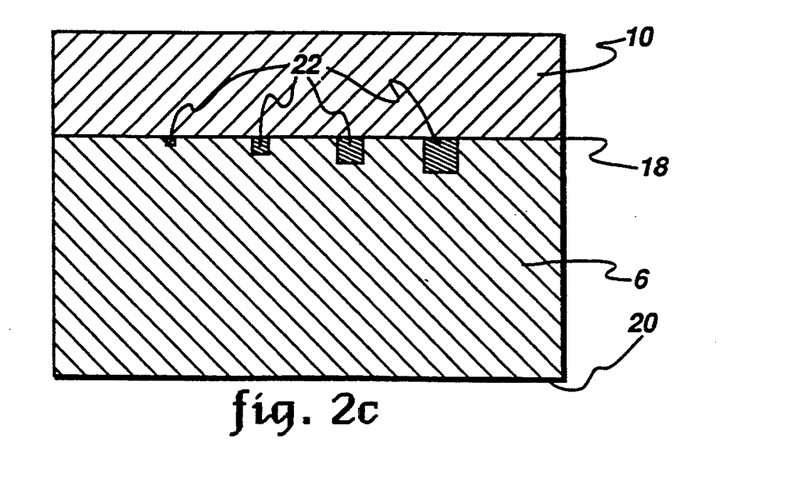
FIG. 2c is a view of the elements of FIG. 2b which further illustrates the method of making and a completed article.

Referring now to FIGS. 2a-2c, a preferred embodiment of an article of the present invention and method of making are described. Referring now to FIG. 2a, an article 2 such as block 4 is prepared by first selecting first alloy preform 6 having a predetermined composition, bonding surface 8 and reference surface 20; and second alloy preform 10 having a predetermined composition and bonding surface 12. In a preferred embodiment, both first alloy preform 6 and second alloy preform 10 are rectangular plates having a predetermined composition of Ti64. In this embodiment, reference surface 20, is located on the side of first alloy preform 6 opposite bonding surface 8, but it could be located on any surface of either first alloy preform 6 or second alloy preform 10. Secondly, a plurality of cavities 14 are formed in bonding surface 8 of first alloy preform 6. In a preferred embodiment, forming comprises machining a matrix of flat-bottomed cylindrical bores having a predetermined size and shape, and orientation and location with respect to reference surface 20, as is described more completely in the examples set forth below. However, it is only necessary that at least one cavity be formed to implement the method of the invention. Also, the step of forming could be part of the step of selecting first alloy preform 6, as by selecting a preform which already includes cavities 14. Thirdly, as illustrated in FIG. 2b, inclusion material 22 having a predetermined composition is placed in cavities 14. In a preferred embodiment, each portion of inclusion material 22 is a preform with a size and shape which correspond to cavity 14 into which it is placed so that inclusion material 22 fills the corresponding cavity 14. In a preferred embodiment, inclusion material 22 comprises Ti—N—O alloys preformed as described more fully in FIGS. 5 and 5a and Example 2 below. Finally, bonding surface 8 of first alloy preform 6 and bonding surface 12 of second alloy preform 10 are placed in touching contact, and a heating means and a pressing means is applied for a time and at a temperature sufficient to form a metallurgical bond between these bonding surfaces. In a preferred embodiment, bonding surfaces are etched prior to the final step in order to improve bonding, as described in Example 2 below. Also in a preferred embodiment, heating and pressing means comprise hot isostatic pressing (HIP) equipment of a type known in the art. The article resulting from the use of the method described is illustrated in FIG. 2c, wherein first alloy preform 6 and second alloy preform 10 are bonded together by bond layer 18 formed by thermal diffusion of at least some of the constituents of first alloy preform 6 and second alloy preform 10 upon application of heat and pressure, and inclusion material 22 is bonded to cavity 14, thereby becoming inclusion 16 and forming synthetic included article 2. Applicants also believe that it should be possible to include a second inclusion (not illustrated) or inclusions in second alloy preform 10 using the same processes described above for inclusion 16. Such an inclusion could also be predetermined with respect to all of the characteristics mentioned for inclusion 16 and located and oriented in relation to reference surface 20 or in relation to a reference surface defined on second alloy preform 10.

Figure 3A:
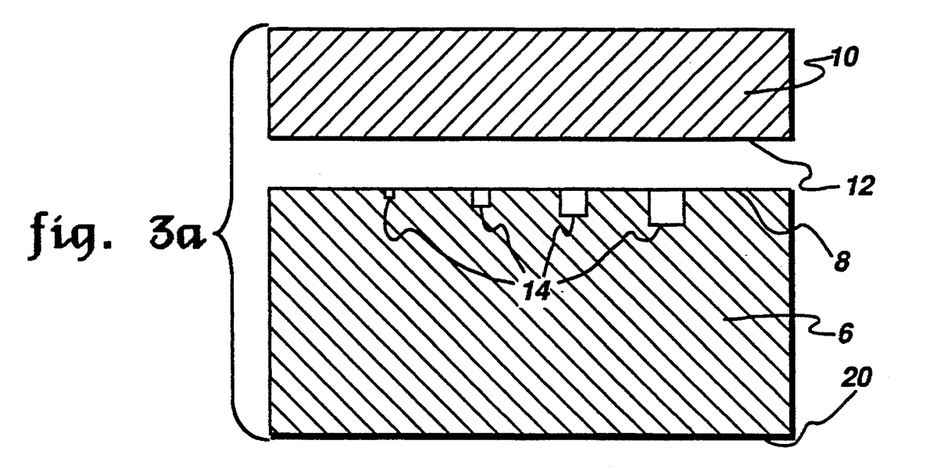
FIG. 3a is an exploded, cross-sectional plan view of certain elements of an article of the present invention which partially illustrate a second embodiment of the method of making.
Figure 3B:
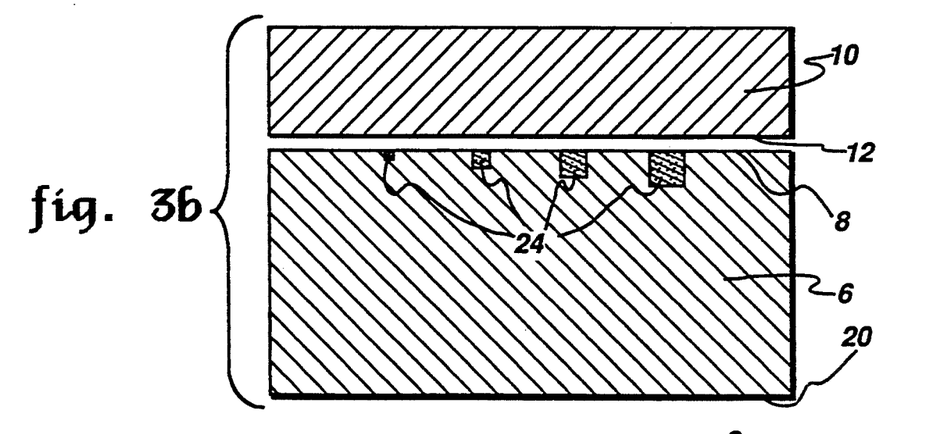
FIG. 3b is a view of the elements of FIG. 3a with certain additional elements and their arrangement which further illustrate a second embodiment of the method of making.
Figure 3C:
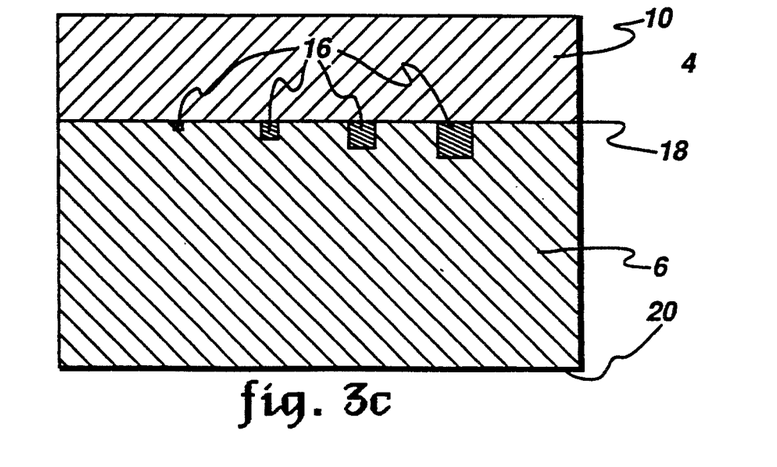
FIG. 3c is a view of the elements of FIG. 3b and their arrangement which further illustrate a second embodiment of the method of making and a completed article.

A second embodiment of an article of the present invention and method of making is illustrated in FIGS. 3a–3c. In this embodiment, the same steps are followed as described above and in reference to FIG. 2a–2c with the exception that inclusion material 24 is placed into cavity 14 in the form of an alloy powder. The alloy powder is compacted and thereby preformed so as to completely fill cavity 14. The bonding time and temperature are selected so as to also densify the packed powder and form inclusion 16 which is both densified and bonded to the walls of cavity 14.

Figure 4A:
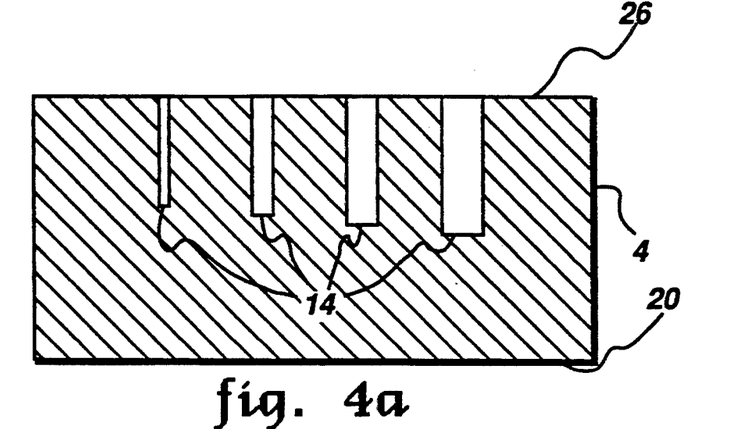
FIG. 4a is an exploded, cross-sectional plan view of certain elements of an article of the present invention which partially illustrate a third embodiment of the method of making.
Figure 4B:
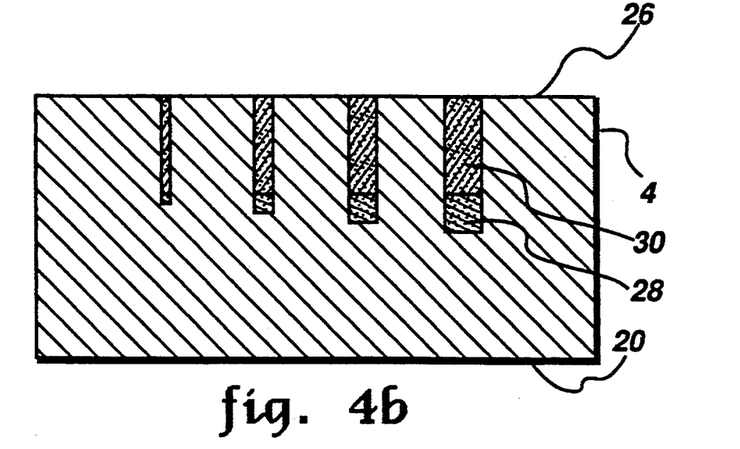
FIG. 4b is a view of the elements of FIG. 4a with certain additional elements and their arrangement which further illustrate a third embodiment of the method of making.
Figure 4C:
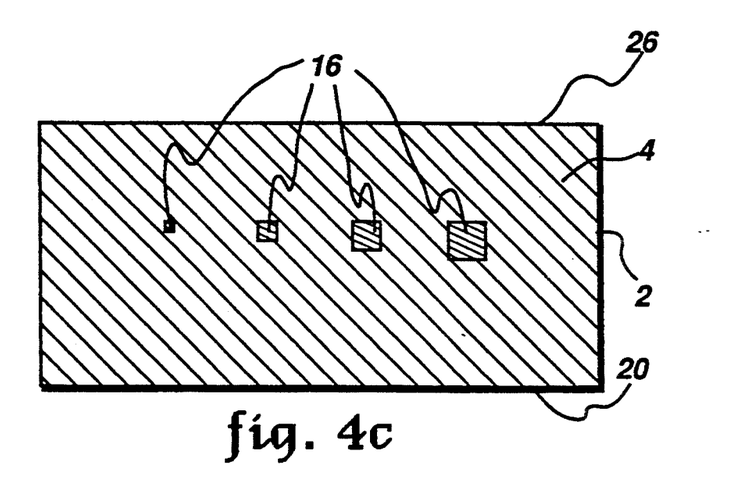
FIG. 4c is a view of the elements of FIG. 3b and their arrangement which further illustrate the method of making.

Applicants believe that a third embodiment is also possible based on the results obtained in the embodiments described above, even though it has not yet been demonstrated. Referring now to FIGS. 4a 4c, an article 2 such as block 4 is prepared by first selecting alloy preform 6 having a predetermined composition, such as Ti64, and a reference surface 20. Secondly, a plurality of cavities 14 are formed in a surface such as top surface 26. In this embodiment, reference surface 20 is located on the side of alloy preform 6 opposite top surface 26. Forming cavities 14 is performed by machining a matrix of flat-bottomed cylindrical bores having a predetermined size and shape, and orientation and location with respect to reference surface 20. However, it is only necessary that at least one cavity 14 be formed to implement the method of the invention. Thirdly, as illustrated in FIG. 4b, inclusion material 28 having a predetermined composition is placed in cavities 14. Inclusion material 28 may be in the form of a preform or powder as described in the embodiments set forth above, except that in this embodiment inclusion material 28 need not completely fill cavity 14, although it may do so, but it should conform completely to that portion of the volume of cavity 14 which it occupies. In the exemplified embodiment, inclusion material 28 may comprise Ti—N—O alloys as described more fully in the examples below. Finally, a heating means and a pressing means is applied for a time and at a temperature sufficient to form a metallurgical bond between inclusion material 28 and alloy preform 6, such as by employing HIP. In an instance, as illustrated in FIG. 4b, where placement of the inclusion material and the desired size and shape of the final inclusion require that inclusion material 28 not completely fill cavity 14, the remainder of cavity 14 may be filled by placing plug 30 comprising in a preferred embodiment the same alloy as alloy preform 6, either in powder form or as a preform, prior to the final step of heating and pressing. The resulting article of the method described in this embodiment is illustrated in FIG. 4c, wherein plug 30 and inclusion material 28 are bonded to cavity 14, thereby forming synthetic included article 2 comprising inclusion 16.

It should be noted that in all of the embodiments, reference surface 20 could be any of the surfaces of either the first or second alloy preforms, depending on the intended use of the finished article. Also, a plurality of reference surfaces 20 could be employed, again depending on the intended use of the finished article. Also, the finished shape of article 2 need not be rectangular, but may be any desired shape.

EXAMPLE 1

Ti—O and TiN Powders Sintered In Situ

In Example 1, blocks of titanium alloy were prepared with synthetic hard-alpha inclusions where the inclusion material used was loose Ti—N—O powder, of known contaminant content, compacted into the cavities and then sintered and densified in situ by HIP.

Blocks of Ti64 alloy with a microstructure typical of an alpha-beta processed material were prepared with inclusions of varied size and composition. Blocks were prepared using the method of the invention as described above and illustrated by FIGS. 3a–3c by HIP of two plates (2.25×2.25×0.50 in. and 2.25×2.25×1.0 in.) which served as the alloy preforms. The larger plate had inclusion material in the form of titanium alloy powder placed in a matrix of small, flat-bottomed, cylindrical bores of varying diameters and depths which had been machined into the bonding surface prior to the HIP process.

Three powder materials were used as inclusion material: (1) "burnt" titanium sponge (−150 mesh), which was pure titanium sponge exposed in air at 950° C. for 2 hours; (2) "burnt" Ti64 powder, (−140 mesh) which was Ti64 powder exposed in air at 950° C. for 2 hours;

and (3) stoichiometric TiN (−325 mesh). The oxygen and nitrogen contents of the burnt sponge are found in Table 1.

TABLE 1

| Material | Powder Compositions | |
|---|---|---|
| | wt. % (at. %) Oxygen | wt. % (at. %) Nitrogen |
| Burnt Ti sponge | 13.6 (31.1) | 1.5 (4.0) |
| Burnt Ti64 powder | 13.9 (29.5) | 3.7 (8.9) |

The general design of the Ti64 block is illustrated in FIG. 1a and FIGS. 3a–3c. The cavities consisted of four identical rows of bores. In each row, there were four bores: 1/32 inch; 1/16 inch; 3/32 inch; and ⅛ inch in diameter. Each bore was flat-bottomed, and as deep as its diameter. The bores of each row were each filled with one of the referenced inclusion materials, with a second row filled with the burnt pure titanium sponge.

The first and second preforms in the form of the plates of Ti64 were cleaned prior to filling them with the inclusion materials in a 30% $HNO_3$-3% HF solution, rinsed in deionized water, and air dried. The cleaning was intended to enhance the bonding of the plates to one another and the inclusions during the HIP process. The inclusion materials in the form of the powders described above were compacted into the bores in each row using small rods of Ti64. While each of the powders was being pressed into a row of bores, the other rows were covered to prevent cross-contamination. After the powder inclusion material was pressed into the bores in each row, excess powder was removed from the face of the plate. After placing inclusion material in all of the bores, the smaller cover plate of Ti64 was placed with its bonding surface facing the bonding surface of the larger plate which contained the inclusion material, and the two pieces were clamped together in pressed contact. The clamped blocks were welded together along their edges by electron beam welding in a vacuum. The welded block was then placed in a hot isostatic press at conditions of 954° C. and 30 ksi for 3 hours.

The completed article, in the form of a rectangular block was examined by ultrasonic inspection techniques developed for identification of hard-alpha inclusions. One as-HIP block was examined metallographically. In this manner the ultrasonic response to the inclusions was compared with their microstructures.

Ultrasonic measurements were consistent with the character of the inclusions as revealed by metallographic sectioning; as-HIP synthetic flaws produced from the burnt powders were well attached to original cavities not fractured or separated from these cavities. Inclusions also appeared to have very little porosity. Metallographic examination also did not indicate the presence of any voids. The signal quality and strength of ultrasonic measurements were consistent with the metallographic results and indicated that the burnt Ti and burnt Ti64 inclusions in the as-HIPped block were intact masses consisting of titanium oxide, titanium metal and some titanium nitride surrounded by an alpha-phase titanium case, rather than voids. The ultrasonic measurements made on these blocks were consistent with theoretical estimates that have been made of the ultrasonic reflectivity of hard-alpha inclusions as compared to voids. Generally, the inclusions showed lower ultrasonic reflectivities than would be expected for voids or cracks of the same size, shape, location and orientation.

Therefore, Applicants conclude that these blocks contain representative inclusions and representative microstructures of hard-alpha titanium. The very consistent nature of all of the TiN and burnt powder inclusions, combined with the very consistent microstructure in the Ti64 material making up the matrix of the blocks indicate that the diffusion bonding process is able to produce the required uncracked inclusions without significantly altering the microstructure of the matrix.

EXAMPLE 2

Pre-sintered Ti/TiN Powder Blends

This example represents a preferred embodiment of the present invention comprising hard-alpha titanium inclusions in Ti64 alloys. Blocks of Ti64 alloy were prepared with synthetic hard-alpha inclusions where the inclusion material was Ti—TiN powder blends, of known contaminant content, which had been previously sintered and densified in a Ti64 alloy can by hot isostatic pressing.

Five compositions were prepared with nominal stoichiometries of: $Ti_2N$ (12.8 w/o nitrogen); $Ti_4N$ (6.8 w/o nitrogen); $Ti_6N$ (4.7 w/o nitrogen); $Ti_8N$ (3.5 w/o nitrogen); and $Ti_{16}N$ (1.8 w/o nitrogen). The powders were blended by rolling mixtures containing the proper stoichiometric quantities of Ti and TiN powders in jars for 20 hours. The powders were placed in Ti64 tubes and processed by HIP at 1400° C. and 30 ksi for 3 hours. The compositions of the resulting densified alloys is shown in Table 2. The Ti—N alloys made from these powder blends also have significant levels of oxygen. The oxygen in these Ti—TiN powder blends appeared to be supplied chiefly by the Ti powder. The analyzed nitrogen levels of the powder blends were below the nominal expected from stoichiometric TiN, but are consistent with the actual composition of the "TiN" used of 43 at. %N ($TiN_{0.75}$).

Oxygen and nitrogen results listed in Table 2 were determined using known techniques. Nitrogen content was determined by acid dissolution and titration; oxygen was determined using a LECO TC-136 oxygen/nitrogen analysis machine.

Figure 5:
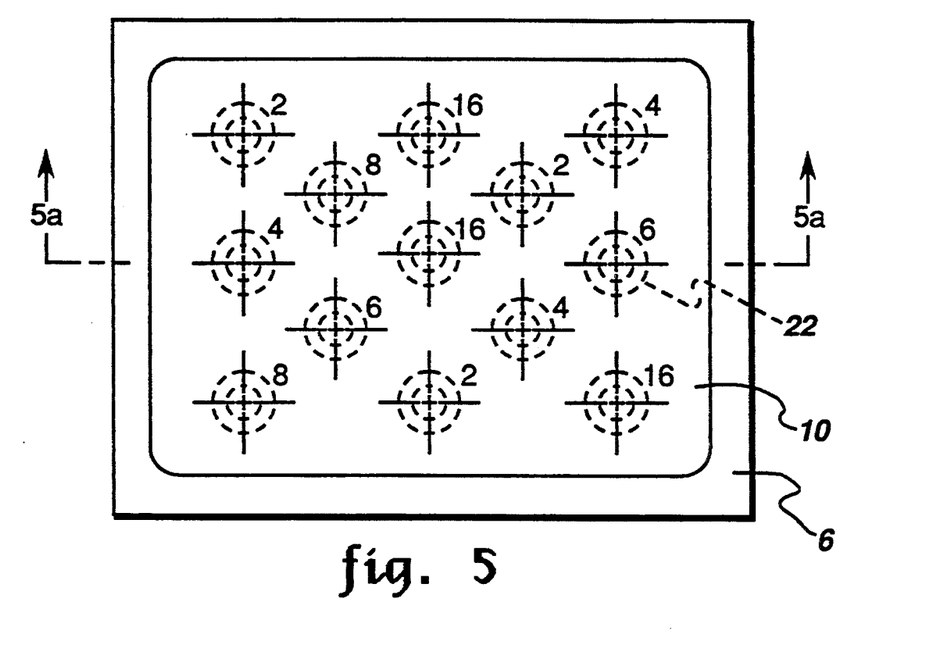
FIG. 5 is a top view of an article of the present invention illustration the arrangement of various Ti—N compositions.
Figure 5A:
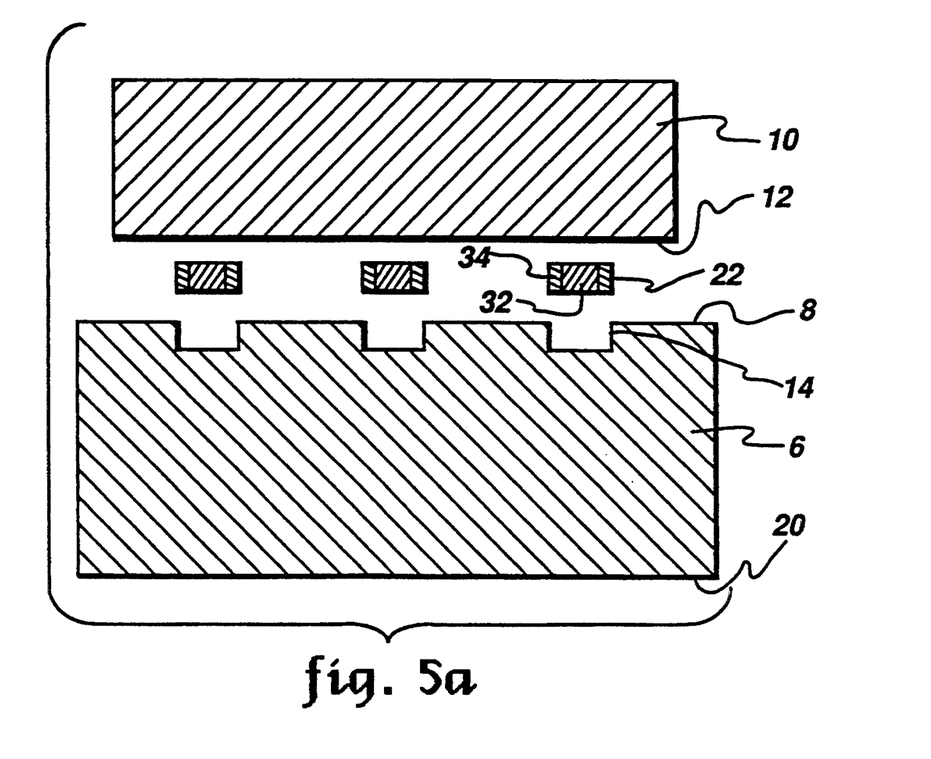

Referring now to FIGS. 5 and 5a and the method illustrated in FIGS. 2a–2c, a 2 in. thick plate 6 of Ti64 was prepared by drilling thirteen 0.375 in. diameter, 0.125 in. deep bores 14 in bonding surface 8 designed to receive inclusion materials 22. As described above, inclusion materials 22 comprise in this example a series of Ti—N alloys 32 and Ti64 tubes 34. Tubes 34 containing the Ti—N alloys 32 were machined to the same diameter, so as to form a slight interference fit with bores 14 and each cut into 0.125 in. thick slices. The diameter of the inclusion material within the Ti64 tubes was approximately 0.16 in. Inclusion material 22 slices were then placed into bores 14. A 1 in. thick Ti64 plate 10 was then clamped and electron-beam welded around the edge with bonding surface 12 facing bonding surface 8 of the plate 6 containing inclusion materials 22, and the assembly was processed by HIP at 955° C. and 30 ksi for 3 hours. FIG. 5 is an illustration of the block as seen looking through the 1 inch plate. The number shown next to the bore is the subscript of the titanium stoichiometry of the inclusion material (i.e. "2" means that the inclusion material was $Ti_2N$, and "16" means $Ti_{16}N$).

Figure 6:
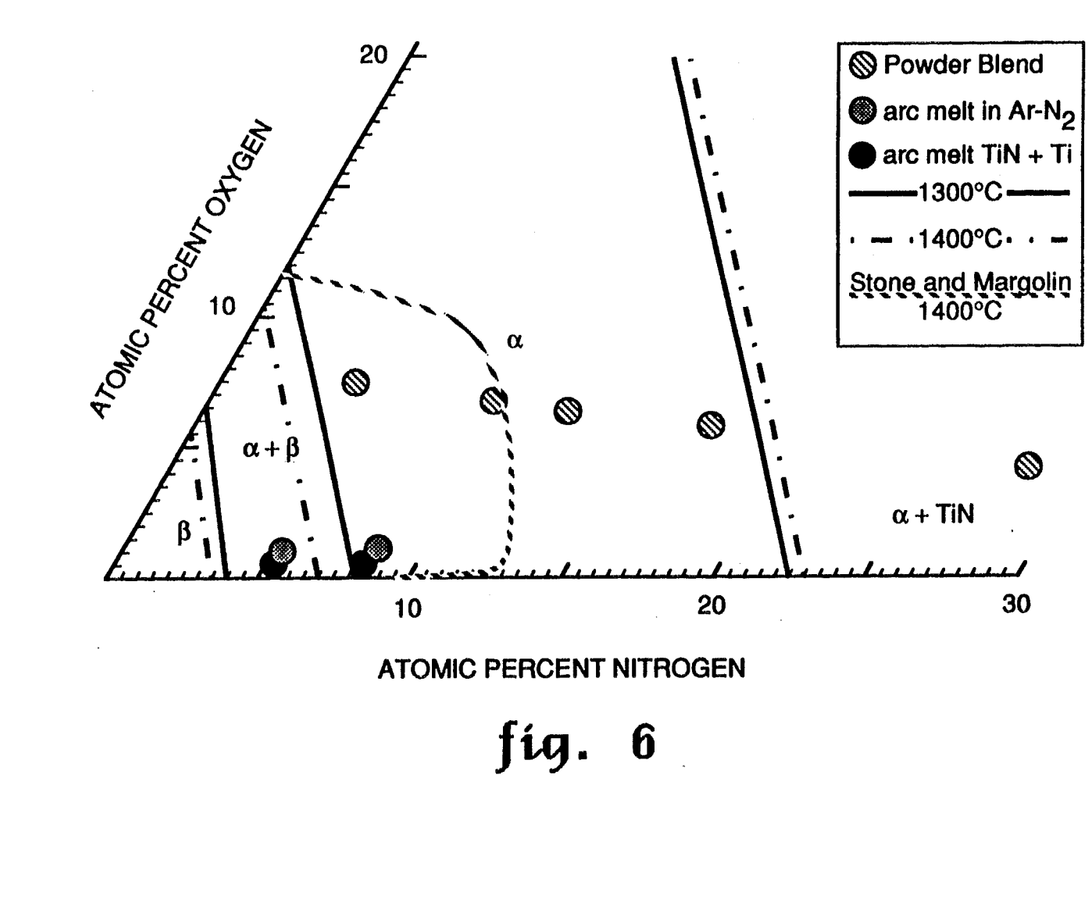
FIG. 6 is a partial ternary phase diagram of the Ti—N—O system indicating Ti—N—O compositions of inclusions prepared in accordance with the method of the present invention.

Referring now to FIG. 6, a ternary Ti—N—O phase diagram was developed from several references. The solvus lines at 1300° C. and 1400° C. were formed both by extensions from the individual binary phase diagrams [Murray 1987], and also from experimental data in which the β phase extends out to about 7.7 at. %N- 6.7 at. %O at 1400° C. [Stone and Margolin 1953]. Using the phase fields drawn from extensions from the binary diagrams, the powder blend alloys of Table 2, "PB8" "PB6" and "PB4" would be in a single phase α field at 1400° C. HIP temperature; and "PB2" would be in the TiN field at 1400° C. HIP. Based on the binary Ti—N diagram, the "PB2" composition should transform from a nitrogen-lean TiN to α+Ti₂N upon cooling. These expected results were confirmed by metallographic examination of PB2, PB4, PB6 and PB8. The experimentally determined α+β field would contain the "PB16" composition. Metallography of "PB16", FIG. 2, revealed a fine grain structure, with a small amount of a second phase, consistent with this composition being in the α+β field near the boundary with the single phase α field. The higher nitrogen composition powder metallurgy alloys appeared as single phases in accordance with expectations based upon the phase diagram. These metallographic results demonstrated that hard-alpha titanium was in fact the starting inclusion material.

Figure 7:
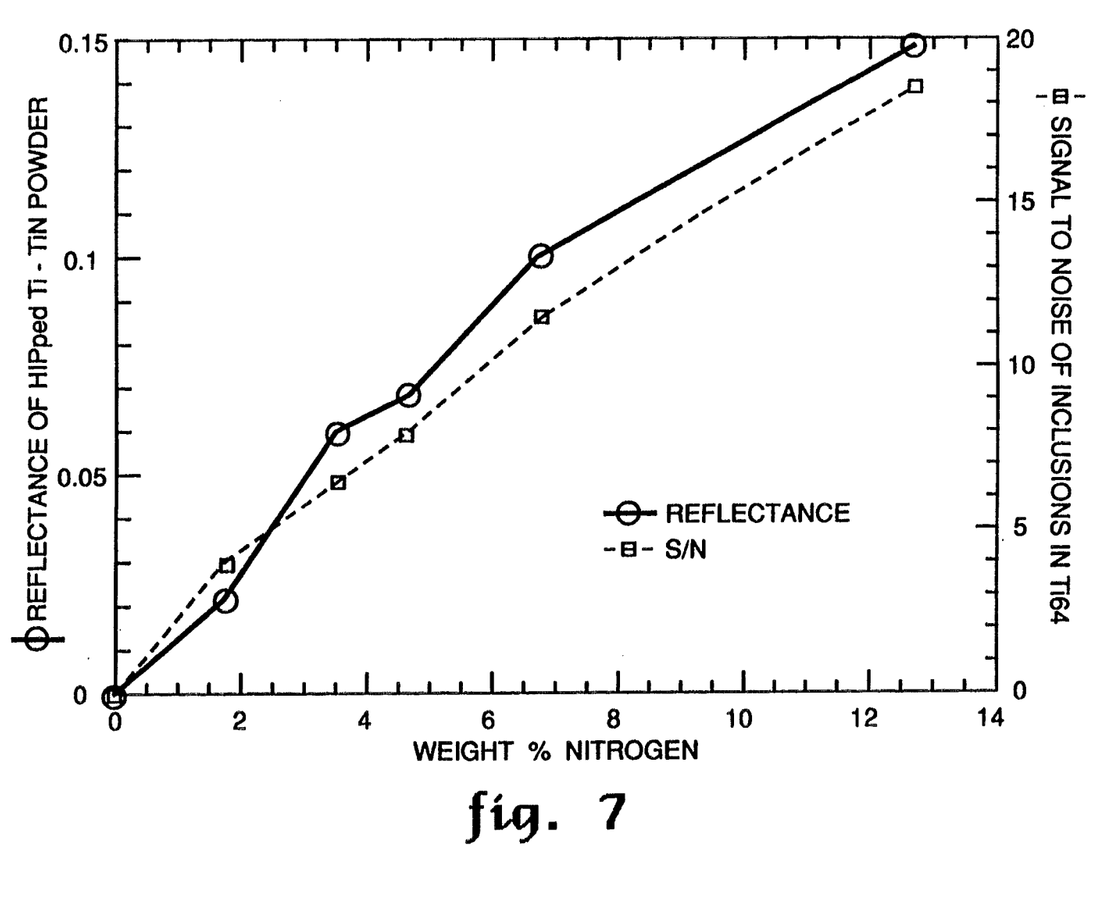
FIG. 7 is a graph displaying both calculated ultrasonic Reflectance and the Signal to Noise Ratio as a function of nitrogen content for Ti—N inclusions in a Ti64 matrix alloy.

Referring now to FIG. 7, the results of two sets of measurements are shown:

(1) Ultrasonic reflectance of HIP processed T-N solid solution inclusion materials before they were sliced and incorporated into the Ti64 plate. Reflectance was calculated from the speed of sound in the inclusion material and its density compared to those of Ti64.

(2) The signal to noise ratio was calculated from the measured ultrasonic reflection of the Ti—N inclusions buried nearly 2 inches in the completed blocks.

These results are significant and indicate a significant advantage because they demonstrate that the physical properties associated with sonic behavior of the starting inclusion material determine the shape of the signal to noise curve measured for actual inclusions within a body. Further, they demonstrate the utility of the subject invention where the nature of the inclusion and that of its surrounding matrix can be varied independently, and a broad range of possible inclusions synthesized and detected.

TABLE 2

Chemical Analysis of Synthetic Hard Alpha

| Material | Preparation Method | Nominal wt. % (at. %) N | Measured wt. % (at. % N | Measured wt. % (at. %) O |
|---|---|---|---|---|
| Ti | Powder | 0.0 | not measured | 2.787 (7.90) |
| TiN | Powder | 22.6 (50.0) | 16.22 (39.50) | 0.586 (1.25) |
| PB2 | Powder Blend | 12.8 (33.3) | 10.73 (28.35) | 1.733 (4.01) |
| PB4 | Powder Blend | 6.8 (20.0) | 5.91 (17.02) | 2.227 (5.62) |
| PB6 | Powder Blend | 4.7 (14.3) | 4.06 (12.11) | 2.427 (6.34) |
| PB8 | Powder Blend | 3.5 (11.1) | 3.11 (9.46) | 2.489 (6.62) |
| PB16 | Powder Blend | 1.8 (5.9) | 1.45 (4.55) | 2.720 (7.48) |
| VAM 1224 | Arc melt in Ar—N₂ | 2.5 (8.1) | 2.72 (8.66) | 0.39 (1.09) |
| VAM 1202 | Arc melt in Ar—N₂ | 1.5 (5.0) | 1.62 (5.30) | 0.34 (0.97) |
| RAM 1228 | Arc melt TiN + Ti | 7.0 (20.5) | 5.88 (17.46) | 0.465 (1.21) |
| RAM 1229 | Arc melt TiN + Ti | 5.0 (15.3) | 3.48 (10.90) | 0.296 (0.81) |
| RAM | Arc melt | 3.5 (11.0) | 2.61 (8.36) | 0.234 (0.66) |

TABLE 2-continued

Chemical Analysis of Synthetic Hard Alpha

| Material | Preparation Method | Nominal wt. % (at. %) N | Measured wt. % (at. % N | Measured wt. % (at. %) O |
|---|---|---|---|---|
| 1234 RAM 1237 | TiN + Ti Arc melt TiN + Ti | 2.0 (6.5) | 1.61 (5.28) | 0.233 (0.67) |

EXAMPLE 3

Arc Melted Ti in a Nitrogen Atmosphere

Blocks of titanium alloy were prepared with synthetic hard-alpha titanium inclusions where the inclusion material was Ti—N in various stoichiometries which was produced by arc melting Ti powder several times in a partial pressure of nitrogen gas, followed by remelting in argon gas to homogenize the ingot.

Two alloy compositions were made by melting titanium powder having the composition shown in Table 2 in a nitrogen atmosphere. First, 333 g of titanium powder was arc melted in a static environment of argon-15 volume % nitrogen. The powder was melted into a small cylindrical button, approximately 3 in. in diameter. The alloy was melted three times in the argon-nitrogen atmosphere. Then, the ingot was remelted three times in an argon atmosphere without nitrogen to homogenize the composition. The metal was weighed before and after each melting step, with the weight change assumed to be due to nitrogen uptake. The ingot was processed by HIP at 1300° C. and 30 Ksi for 3 hours to close up any voids and cracks remaining from the melting process and to further homogenize the composition. Two ingots were made in this manner; one was estimated to contain 5.1 wt. % nitrogen, the other 4.4 wt. % nitrogen.

These nitrogenated ingots were cut into pieces and re-melted with titanium powder to produce two further ingots, with intended compositions of 2.5 and 1.5 wt. % nitrogen (8.1 and 5.0 at. %), based on the assumed compositions of the nitrogenated ingot. These ingots were then re-melted in an argon atmosphere three times each, with the ingot flipped each time. The ingots were again processed by HIP at 1300° C. and 30 Ksi for 3 hours to close voids and cracks and homogenize the composition. The resulting measured compositions are shown in Table 2 as VAM 1224 and VAM 1202. The low nitrogen ingot melting composition, VAM 1202, would lie well into the α+β field of the phase diagram shown in FIG. 7 at a 1300° C. HIP temperature. VAM 1224 would lie near the border of the α+β and the all-α fields.

Blocks containing inclusions of the arc melted Ti—N—O alloys were produced in a similar way as described for Example 2. A matrix of flat-bottomed bores were drilled in a Ti64 plate and pins of corresponding diameter Ti—N—O alloys were placed in the bores. The pins were produced by traveling wire electro-discharge machining (edm) followed by etching in a solution of 30% nitric acid, 10% hydrofluoric acid to remove any microstructural effects caused by the machining process. The use of arc melted Ti—N—O material permitted much smaller diameter inclusions than used in Example 2. A Ti64 plate to receive the hard alpha inclusions of VAM 1202 was made with four rows of four bores of: 0.032 in. diameter, 0.032 in. depth; 0.047 in. diameter, 0.047 in. depth; 0.062 in. diameter, 0.062 in. depth; and 0.078 in. diameter, 0.078 in. depth. Two plates of Ti64 were also made with four rows of bores, each made to receive sixteen pins of the same diameter, each row having pins representing one of the four bore sizes described above. Into one plate were placed pins made from VAM 1202, and into the other pins made from VAM 1224. After electron-beam welding 1 in. thick Ti64 cover plates over the pins on all blocks, the attached plates were processed by HIP at 900° C. and 15 ksi for 3 hours. This also resulted in monolithic Ti64 blocks containing uncracked synthetic Ti—N—O inclusions of VAM 1202 and VAM 1224 which were bonded to the sidewalls of the cavities into which they had been placed. Such blocks could be used to study detection of hard-alpha titanium inclusions using ultrasound as a function of inclusion size.

EXAMPLE 4

Arc Melted Ti/TiN Powder

Blocks of titanium alloy were prepared with synthetic hard-alpha titanium inclusions where the inclusion material was Ti—N in various stoichiometries produced by arc melting Ti powder together with selected amounts of TiN powder.

Compositions of an inclusion material were prepared by arc melting mixtures of Ti powder and TiN powder in an argon atmosphere. The resulting ingots were melted three times, flipping the ingot over after each melt. After melting, the ingots were processed by HIP at 1300° C. and 30 ksi for 3 hours. The aim compositions were 7 wt. % (20.5 at. %), 5 wt. % (15.3 at. %), 3.5 wt. % (11.0 at. %) and 2.0 wt. % (6.5 at. %) nitrogen based on the assumption that the starting TiN powder was stoichiometric, i.e., contained 22.63 weight % nitrogen. The resulting compositions are shown in Table 2 as RAM 1237, RAM 1234, RAM 1229, and RAM 1228. The low nitrogen ingot melting composition, RAM 1237 would lie well into the $C\alpha+\beta$ field at 1300° C. HIP temperature. RAM 1228 would lie near the border of the $\alpha+\beta$ and the all-$\alpha$ fields. RAM 1229, and RAM 1234 would be in an all-$\alpha$ field.

Blocks containing inclusions of the arc melted Ti—N—O alloys were produced using the same method as described for Example 3, except that the plates and pins were of slightly different sizes. Inclusions made from arc melted Ti—TiN compositions were HIP bonded into blocks under similar conditions as described in Example 3. The plates bored to receive pins were 1 in. thick and contained an array of four 0.078 in. diameter, 0.075 deep cavities. Pins 0.075 in. diameter and 0.075 in.long prepared as in Example 3 were cut from each of the four Ti—N—O materials and placed in separate plates. Cover plates 0.50 in. thick were attached to the plates containing the pins, with the bonding surfaces on the plates facing one another, as described above. The attached plates were processed by HIP at 900° C. and 15 ksi for 3 hours. The result was a monolithic Ti64 block containing uncracked inclusions of the compositions described in Table 2 which were bonded to the sidewalls of the cavities into which they had been placed. The finished blocks could be used to study the detectability of Ti—N—O inclusions as a function of inclusion chemistry.

The examples provided above in conjunction with this detailed description of the invention are only representative of preferred embodiments of the invention with respect to hard-alpha titanium inclusions and Ti64 alloys, and are not intended to limit the scope of the invention or claims to only oxide/nitride base inclusions, or to Ti-base alloys.

What is claimed is:

1. A method for forming a titanium alloy preform having a reference surface and containing at least one metallic inclusion having a predetermined composition, shape and size and also having a predetermined orientation to and location from the reference surface, comprising the steps of:

selecting a first titanium alloy preform and a second titanium alloy preform each having a predetermined composition of alloying constituents and a bonding surface, wherein at least one of the first alloy preform and the second alloy preform have at least one reference surface;

forming at least one cavity having a predetermined size and shape in the first titanium alloy preform;

placing an inclusion material selected from the group consisting of a nitride, oxide, or carbide of titanium, or any combination thereof, and having a predetermined composition into the cavity;

placing the bonding surfaces of the first titanium alloy preform and the second titanium alloy preform in touching contact; and applying a means for heating and a means for pressing to the first titanium alloy preform the second titanium alloy preform and the inclusion material together for a time sufficient to form an inclusion and a metallurgical bond between the inclusion and the first titanium alloy preform and between the bonding surfaces of the first titanium alloy preform and the second titanium alloy preform wherein the inclusion has a predetermined orientation to and distance from the at least one reference surface.

2. A method for forming a titanium alloy preform having a reference surface and containing at least one metallic inclusion having a predetermined composition, shape and size and also having a predetermined orientation to and location from the reference surface, comprising the steps of:

selecting a titanium alloy preform having a predetermined composition of alloying constituents and at least one reference surface;

forming at least one cavity having a predetermined size and shape in the alloy preform at a predetermined orientation to and distance from the reference surface;

placing an inclusion material selected from the group consisting of a nitride, oxide or carbide of titanium, or any combination thereof, and having a predetermined composition into the cavity; and applying a means for heating and a means for pressing to the titanium alloy preform and the inclusion material for a time sufficient to form an inclusion and a metallurgical bond between the inclusion and the titanium alloy preform.

3. The method of claim 2, further comprising the step of placing a plug over the inclusion material and within the cavity, wherein said placing a plug is performed after said placing art inclusion material, but prior to said applying a means for heating and a means for pressing.

4. The method of claim 3, wherein the plug comprises a titanium alloy powder.

5. The method of claim 4, wherein the titanium alloy powder has a composition that is the same as the composition of the titanium alloy preform.

6. The method of claim 3, wherein the plug comprises a preformed titanium alloy.

7. The method of claim 6, wherein the preformed titanium alloy plug has a composition that is the same as the composition of the titanium alloy preform.

8. The method of claim 1, further comprising the step of: forming at least one cavity having a predetermined size and shape in the second titanium alloy preform, wherein said forming is done prior to said placing an inclusion material, and wherein said placing an inclusion material further comprises placing an inclusion material into the at least one cavity of the second titanium alloy preform.

9. The method of claim 1, further comprising the step of: etching the cavity and the bonding surfaces of the first titanium alloy preform, wherein said etching is performed after said forming at least one cavity and before said placing an inclusion material.

10. The method of claim 8, further comprising the step of: etching the cavities and the bonding surfaces of both the first titanium alloy preform and the second titanium alloy preform, wherein said etching is performed after said forming of cavities in the first and second titanium alloy preforms and before said placing an inclusion material.

11. The method of claim 2, further comprising the step of: etching the cavity and the bonding surfaces of the titanium alloy preform, wherein said etching is performed after said forming at least one cavity and before said placing an inclusion material.

* * * * *